United States Patent [19]

Chasin et al.

[11] Patent Number: 4,818,679
[45] Date of Patent: Apr. 4, 1989

[54] METHOD FOR RECOVERING MUTANT CELLS

[75] Inventors: Lawrence A. Chasin; Gail U. Chasin, both of Leonia, N.J.

[73] Assignee: The Trustees of Columbia University in the City of New York, New York, N.Y.

[21] Appl. No.: 702,958

[22] Filed: Feb. 19, 1985

[51] Int. Cl.$^4$ .................. C12Q 1/68; C12Q 1/26; C12Q 1/06; C12Q 1/04

[52] U.S. Cl. .................................. 435/6; 435/25; 435/34; 435/39; 435/172.1; 935/77

[58] Field of Search .............. 435/6, 25, 172.1, 30, 435/34, 39; 935/77, 82

[56] References Cited

U.S. PATENT DOCUMENTS

4,345,027  8/1982  Dolbeare ........................... 435/21
4,649,109  3/1987  Perlman ............................ 435/30

OTHER PUBLICATIONS

Urlaub, G. et al., "Use of Fluorescence-Activated Cell Sorter to Isolate Mutant Mammalian Cells Deficient in an Internal Protein, Dihydrofolate Reductase"; *Somatic Cell and Molecular Genetics;* vol. 11, No. 1, (Jan., 1985), pp. 71–77.

Urlaub, G. et al., "Isolation of Chinese Hamster Cell Mutants Deficient in Dihydrofolate Reductase Activity"; *Proc. Natl. Acad. Sci., U.S.A.,* vol. 77, No. 7, (1980), pp. 4216–4220.

Urlaub, G. et al.; "Deletion of the Diploid Dihydrofolate Reductase Locus from Cultured Mammalian Cells", *Cell,* vol. 33, (Jun., 1983), pp. 405–412.

Kaufman, R. J. et al.; "Quantitation of Dihydrofolate Reductase in Individual Parental and Methotrexate Resistant Cells"; *J. Biol. Chem.,* vol. 253, No. 16, (1978), pp. 5852–5860.

Miller, A. G. et al.; "Novel Variants in Benzo($\alpha$)pyrene Metabolism"; *J. Biol. Chem.,* vol. 256, No. 5, (1981), pp. 2433–2437.

*Primary Examiner*—Elizabeth C. Weimar
*Attorney, Agent, or Firm*—John P. White

[57] ABSTRACT

This invention concerns a method for recovering mutant cells which produce a substance in a quantifiably reduced amount relative to wild type cells, and the mutant cells so recovered. The method involves contacting the mutant cells under suitable conditions with a suitable amount of an appropriate detectable compound capable of binding to the substance when it is present in the cells so as to permit the detectable compound to bind to the substance. The amount of the detectable compound bound to the substance in the cells is then detected, and the cells which produce the substance in the quantifiably reduced amount are thereby detected. Such cells which produce the quantifiably reduced amount of the substance are then recovered. This invention is applicable to a wide variety of cell types of various genetic characteristics and should therefore be useful in providing a wide range of useful mutant cells.

19 Claims, 1 Drawing Sheet

METHOD FOR RECOVERING MUTANT CELLS

This invention was made with government support under grant number GM 22629 from the National Institutes of Health, United States Department of Health and Human Services. The government has certain rights in this invention.

BACKGROUND OF THE INVENTION

Throughout this application various publications are referenced by arabic numerals within parantheses. Full citations for these publications may be found at the end of the specification immediately preceding the claims. The disclosures of these publications in their entireties are hereby incorporated by reference into this application in order to more fully described the state of the art to which this invention pertains.

The isolation of mutant clones from cultured mammalian cell lines usually relies on the application of a selective growth condition under which the mutant cells can grow while the wild type cells cannot. In some cases, however, the mutant phenotype does not present an obvious growth advantage that can be exploited toward this end. An alternative method for recognition of mutant cells has been the differential staining of mutant colonies under conditions where the cells remain viable (e.g., the immunoprecipitation of secreted products into a surrounding agar medium (1, 2)). Often the staining procedure involves cell fixation; in these cases sib selection (3) or replica plating (4, 5) has been used to isolate the viable mutant cells. In certain of these prior methods a portion of the mutant cells are exposed to conditions under which the desired mutant cells cannot survive. By killing a portion of the mutant cells the occurrence of the desired mutation is confirmed. The advent of the fluorescence-activated cell sorter (FACS) has provided a less costly, more convenient and more direct way to recover mutant cells from amongst much larger populations of mutagenized cells than can be screened at the colonial level. Provided that the mutant cells can be distinguished from wild type with a fluorescent reagent, large numbers (millions) of individual cells, rather than colonies, can be screened. The sorted population that results can be greatly enriched in mutant cells. FACS sorting has been applied primarily to the isolation of cell populations of different development status. Most mutants or variants that have been isolated with this technique have been those affected in the expression of cell surface proteins (see ref. 6 for a review). One exception has been the selection of nonclonal subpopulations of a mouse hepatome cell line exhibiting increasd or decreased rates of aromatic hydrocarbon metabolism (7). In one embodiment of the invention described herein, the FACS technique has been applied for the isolation of mutant mammalian cells that are devoid of dihydrofolate reductase, an internal enzyme.

The isolation by a selective matabolic method of mutant Chinese hamster ovary (CHO) cells lacking dihydrofolate reductase (DHFR) activity, i.e. lacking a functional dhfr gene, has been described previously (8, 9). There, the mutant cells were obtained form CHO cells which were functionally heterozygous with respect to the dhfr gene. Under the appropriate growth conditions DHFR-deficient cells are perfectly viable. Moreover, they can be selected from amongst large populations of functionally heterozygous wild type cells by killing the latter with a tritiated deoxyuridine suicide technique (8). While it is expensive and labor intensive, this selective growth technique works well for selecting mutants from mutagenized populations where their frequency is higher than $10^{-6}$. However, because even moderate cell densities interfere with this selection (10), a large number of cells must be employed at a low cell density. Thus the selective growth technique represents a relatively costly and laborious procedure for the selection of spontaneous mutants, which occur at a frequency on the order of $10^{-7}$. Accordingly, the selective growth technique would be impractical for recovery in a single step of mutant cells containing a double mutation, e.g. for recovering mutant cells lacking DHFR activity (i.e. lacking a single functional dhfr gene) directly from mutagenized wild type cells which are functionally deploid with respect to the dhfr gene (i.e. containing two functional dhfr genes). Such an approach would certainly be impractical and most likely unsuccessful based on previous attempts (8). Therefore, the practical utility of the selective growth method depends on the availability of wild type cells which are functionally hemizygous or heterozygous with respect to the gene to be mutated. Often such cells are not available. Moreover, the isloation of such cells by selective growth methods is extremely difficult, requiring additional manipulations, and has not proven to be readily reproducible.

A FACS technique was therefore investigated as a more practical, more reliable and more widely applicable means of selecting or enriching for mutants which are either devoid of DHFR activity, i.e. contain no functional copy of the gene, or are functionally hemizygous or heterozygous with respect to the dhfr gene, i.e. contain one functional copy of the gene. Kaufman et al. (11) had shown that a fluroescent derivative of methotrexate could be used in the analysis and separation of cells that contained elevated levels of DHFR due to gene amplification. Methotrexate is a substrate analog that binds to DHFR with high affinity. After treatment with fluoresceinated Methotrexate, the stoichiometric binding of the drug provides an accurate indicator of the number of DHFR molecules per cell (11). Preliminary experiments by others had also indicated that the low level of fluorescence yielded by wild type CHO cells carrying two diploid copies of the dhfr gene could be distinguished from the background value exhibited by a mutant lacking DHFR activity, i.e. carrying no function copies of the dhfr gene (8). The aforementioned preliminary experiments did not involve CHO cells carrying a single copy of the dhfr gene, i.e. functional hemizygotes or heterozygotes, and no mutant cells were recovered. In the present invention, mutant cells containing no copy, a single copy or two copies of a gene, e.g. the dhfr gene, can be distinguished by the FACS. This instrument can be used by the method of this invention to recover mutant cells containing a single functional gene copy as well as mutant cells devoid of activity associated with the gene, i.e. containing no functional copy of the gene.

SUMMARY OF THE INVENTION

This invention concerns a method for recovering mutant cells, e.g. mammalian mutant cells, which produce a substance, e.g. a protein such as an enzyme within the cells, in a quantifiably reduced amount, e.g. about fifty percent (50%) or less than about ten percent (10%), relative to wild type cells, i.e. relative to wild type cells grown under the same conditions. The method involves contacting the mutant cells under suitable conditions with a suitable amount of an appropriate detectable compound, e.g. a fluorescent compound, capable of binding to the substance when it is present in the cells so as to permit the detectable compound to bind to the substance. The amount of the detectable compound bound to the substance in the cells is then detected, and the cells which produce the substance in the quantifiably reduced amount are thereby detected. Such cells which produce the quantifiably reduced amount of the substance are then recovered.

Mutant cells of this invention may be produced by treating wild type cells under mutaganizing conditions with a mutagen so as to produce mutant cells, including mutant cells which produce a substance in a quantifiably reduced amount relative to wild type cells. Such mutant cells may then be contacted with the detectable compound as stated above.

This method may be employed with a wide variety of cell types such as procaryotic or eucaryotic cells and haploid or diploid cells, including homozygous, heterozygous and hemizygous cells.

Thus, where the gene which results in the production of the substance is allelic, the mutant cells recovered in one embodiment are characterized by a mutation in one allele and the quantifiably reduced amount of the substance produced by the mutant cells is about 50% of the amount produced by wild type cells. In other embodiments the mutant cells are characterized by mutations at both alleles or at the single functional gene for the production of the substance. In these embodiments, the quantifiably reduced amount of the substance produced by the mutant cells is less than about 10% of the amount produced by the wild type cells.

In a further embodiment, mutant cells which produce less than about 10% of the amount of the substance produced by the wild type cells may be obtained from previously recovered cells producing about 50% of the amount of the substance produced by the wild type cells. This embodiment involves culturing the mutant cells under selective growth conditions.

An appropriate detectable compound capable of binding to the substance is one which is detectable by any of the conventional methods e.g. ultraviolet absorption, fluorescence, chemiluminescence, etc. In a presently preferred embodiment the detectable compound is fluorescent.

It is also preferable that the above-mentioned steps of detecting and recovering be automated, e.g. with an automated cell sorting apparatus such as a fluorescence activated cell sorter (FACS).

In addition to the above-described methods, this invention also concerns the mutant cells so recovered which may be mammalian cells, preferably of non-tumorigenic cells lines and especially wherein the mutants contain a reduced amount of a substance produced by an amplificable gene. The mutant cells may contain a mutation in a gene present in a single copy, or in one or both alleles of a pair of alleles associated with the production of the substance.

DETAILED DESCRIPTION OF THE INVENTION

Figure 1:
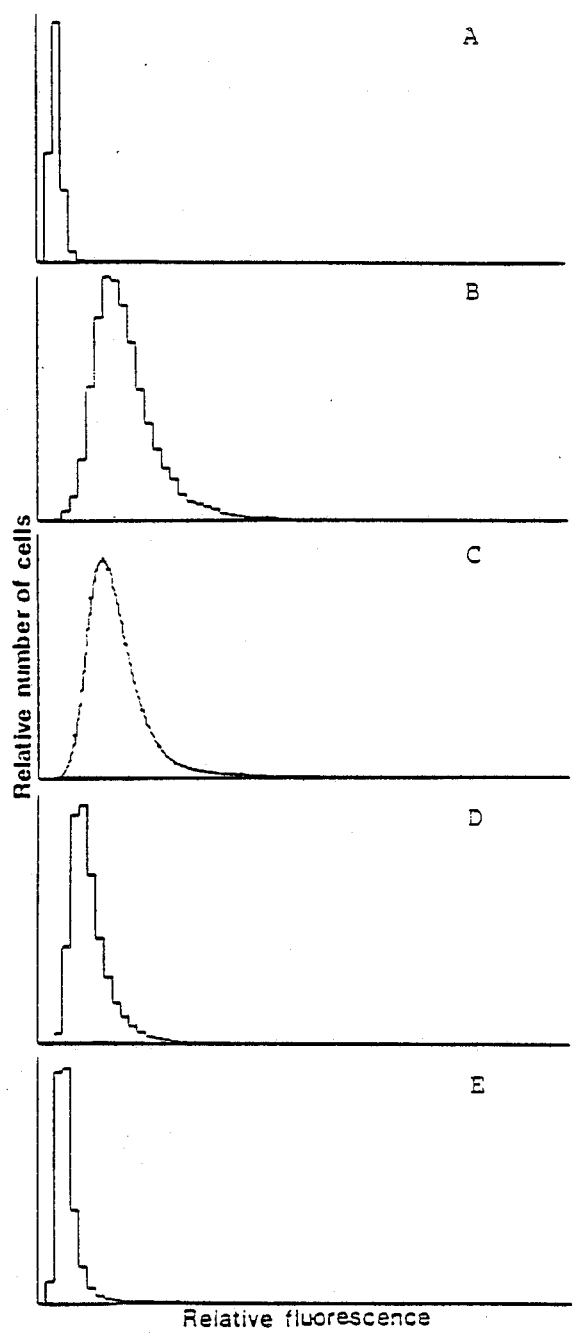
FIG. 1 FACS fluorescence distribution of CHO cells treated with F-MTX. Cells were exposed to F-MTX and sorted as described hereinafter in Materials and Methods. The abscissa indicates relative fluorescence per unit cell volume (in arbitrary units). Cell volume was taken to be proportional in the light scattering signal. The ordinate gives the number of cells in the population that exhibit the value indicated on the abscissa. Panel A, untreated DG21 (dhfr-negative) cells. All fluorescence here is due to autofluorescence background. The cells in all other panels have been treated with F-MTX. B-E, mutagenized UA21 cells after 0, 5, 6, and 7 sorts.

As stated above, this invention concerns a method for recovering mutant cells which produce a substance in a quantifiably reduced amount relative to wild type cells, i.e. relative to wild type cells grown under the same conditions. The method involves contacting the mutant cells under suitable conditions with a suitable amount of an appropriate detectable compound capable of binding to the substance when it is present in the cells so as to permit the detectable compound to bind to the substance. The amount of the detectable compound bound to the substance in the cells is then detected, and the cells which produce the substance in the quantifiably reduced amount are thereby detected. Such cells which produce are quantifiably reduced amount of the substance are then recovered.

In accordance with this invention, wild type cells may be treated under mutagenizing conditions with a mutagen so as to produce mutant cells, including mutant cells which produce a substance in a quantifiably reduced amount relative to wild type cells. such mutant cells may then be contacted with the detectable compound as stated above. By "wild type cells", as the term is used herein, is meant cells in which the mutation resulting in the production of the substance in a quantifiably reduced amount has not occurred. In a preferred embodiment wild type cells are treated under mutagenizing conditions with the mutagen N-acetoxy-N-2-acetyl-aminofluorine (NAAAF), although other conventional materials and methods, including irradiation, are also suitable for mutagenesis in this and other embodiments.

This method may be employed with a wide variety of cell types such as procaryotic or eucaryotic cells and haploid or diploid cells, including homozygous, heterozygous and hemizygous cells. In one embodiment the quantifiably reduced amount of the substance produced by the mutant cells is about fifty percent (50%) of the amount produced by the wild type cells under the same growth conditions. In another embodiment the quantifiably reduced amount is less than about ten percent (10%) of the amount produced by the wild type cells under the same growth conditions.

Thus, where the gene which results in the production of the substance is allelic, the mutant cells recovered in one embodiment are characterized by a mutation in one allele and the quantifiably reduced amount of the substance produced by the mutant cells is about 50% of the amount produced by wild type cells. In another embodiment the mutant cells are characterized by mutations at both alleles, and the quantifiably reduced amount of the substance produced by the mutant cells is less than about 10% of the amount produced by the wild type cells.

One embodiment for recovering mutant cells producing less than about 10%, relative to the wild type cells, of a substance which is produced as a result of an allelic gene involves first recovering by the previously described method mutant cells which produce about 50% of the amount of the substance produced by the wild type cells. Suitably, the mutant cells which produce about 50% of the amount of the substance may be produced using a mutagen, e.g. NAAAF, as previously described. The mutant cells so recovered are then treated with a mutagen under mutagenizing conditions so as to provide mutant cells which produce the substance in an amount less than about 10% of the amount produced by the wild type cells. The mutant cells so produced may then be recovered as follows: first, the mutant cells may be contacted with a suitable amount of an appropriate detectable compound of binding to the substance when it is present in the cells so as to permit the detectable compound to bind to the substance. The amount of the detectable compound bound to the substance in the cells may then be detected, and the mutant cells which produce less than about 10% of the amount of the substance produced by the wild type cells may thereby be detected. The mutant cells so produced and detected may then be recovered.

Alternatively, the mutant cells which produce less than about 10% of the amount of the substance produced by the wild type cells may be recovered by culturing the mutagenized cells under conditions selective for the desired mutant cells. In this method the mutagenized cells are cultured under suitable conditions for the growth of the mutant cells which produce less than 10% of the amount of the substance produced by the wild type cells, the suitable conditions being such that other cells, e.g. wild type cells or cells which produce about 50% of the amount of the substance produced by the wild type cells do not survive. After a suitable period of time for selective growth of the desired mutant cells, the desired mutant cells, i.e. those which produce less than about 10% of the amount of the substance relative to the wild type cells, are harvested and thereby recovered.

In another embodiment the gene which results in production of the substance is present in a single functional gene copy, e.g. is nonallelic. The mutant cells recovered in this embodiment are characterized by a mutation in the gene, and the quantifiably reduced amount of the substance is less than about 10% of the amount produced by the wild type cells.

As previously indicated the methods of this invention are not limited to any specific cell type. Mammalian cells are preferred, however, because of the utility of mutant mammalian cells in a variety of genetic engineering applications. Suitable mammalian cells include e.g. Chinese hamster ovary cells, especially non-tumorigenic cells such as African green monkey kidney cells (Vero cells).

In accordance with this invention the substance to which the detectable compound binds may be a protein within the cells such as an enzyme, e.g. dihydrofolate reductase. Suitably, the substance may be any substance which is not essential for cell viability and to which an appropriate detectable compound is capable of binding. Presently preferred, however, is an embodiment in which the gene which results in production of the substance in the cells is amplifiable, since mutants lacking a functional amplifiable gene are of great utility in numerous genetic engineering applications.

At present, dihydrofolate reductase, encoded for by the amplifiable dhfr gene, is a preferred substance.

An appropriate detectable compound capable of binding to the substance is one which is detectable by any of the conventional methods e.g. ultraviolet absorption, fluorescence, chemiluminescence, etc. In a presently preferred embodiment the detectable compound is fluorescent. In an especially preferred embodiment the detectable compound is a fluorescent derivative of methotrexate, e.g. a derivative containing a fluorescein or rhodamine moiety, the derivative being capable of binding to dihydrofolate reductase under suitable conditions. Alternatively, where the substance is an enzyme the detectable compound may be a fluorogenic substrate of the enzyme.

The method of this invention may also be useful for recovering mutant cells deficient in mitochondrial ATPase. Such mutants may be selected by using as the detectable compound aurovertin, a fluorescent inhibitor of the respiratory enzyme which is capable of binding to the enzyme. The method may also be used to recover mutant cells having a quantifiably reduced enzyme level relative to wild type cells. In this embodiment the detectable compound may be a flourescent cofactor, e.g. FAD, which binds to abundant enzymes such as succinic dehydrogenase or lipoamide dehydrogenase. In a further embodiment the method might be useful to recover hybridoma cells producing specific monoclonal antibodies. In this embodiment the detectable compound may be a relatively low molecular weight fluorescent hapten to the monoclonal antibody. The hapten must be small enough to enter the hybridoma cells where it must also be capable of binding to the internal pool of immunoglobulin molecules. Mutant hybridoma cells producing monoclonal antibodies no longer capable of binding the hapten, or capable of binding the hapten more avidly or less avidly might be recovered by contacting the mutant cells with relatively low concentrations of the fluorescent hapten, and following the method of this invention described above to detect and recover cells based upon the amount of hapten bound therein.

It is preferably in practicing the various embodiments of this invention that the above-mentioned steps of detecting and recovering be automated, e.g. with an automated cell sorting apparatus such as a fluorescence activated cell sorter (FACS).

Typically, the mutant cells so isolated may be cultured to produce cell progeny and cells of the progeny so produced resubjected at least once, and preferably one to eight times, to the recovery method. The optimal number of repetitions will depend on the choice of wild type cells and on the selectivity with which the mutant cells are recovered, which in turn depends on factors such as cell density and the signal to noise ratio during the detection step, etc.

In addition to the above-described methods, this invention also concerns the mutant cells so recovered. As previously indicated mutant mammalian cells are preferred, preferably of non-tumorigenic cell lines such as African green monkey kidney cells, and especially wherein the mutants contain a reduced amount of a substance such as DHFR produced by an amplifiable gene. The mutant cells may contain a mutation in a gene present in a single copy, or in one or both alleles of a pair of alleles associated with the production of the substance.

The experimental details which follow are set forth to illustrate the invention. The experimental details are not intended to, and should not be construed to, limit in any way the invention as claimed hereinafter. While the Experiment which follows involves hemizygote Chinese hamster ovary cells as the wild type cells, the enzyme dihydrofolate reductase as the substance which is produced in a quantifiably reduced amount in the mutant cells, fluoresceinated methotrexate as the detectable compound, NAAAF as th emutagen, and mutant cells lacking DHFR activity, i.e. containing no functional dhfr gene, it should be understood that this experiment is provided merely in the way of example, and that as previously disclosed the method of this invention is widely applicable, e.g. to various other cell types, substances produced therein, detectable compounds, methods of mutagenesis and mutant cell types so recovered.

EXPERIMENTS

Materials and Methods

Cell Culture. The dhfr-positive cell line that served as the starting point for the induction and isolation of dhfr-deficient mutants was clone UA21, a hemizygote Chinese hamster ovary cell line that carries only a single copy of the dhfr gene (9). Cells were grown in modified (12) F12 medium supplemented with 10% (v/v) fetal calf serum (Gibco). This serum was exhaustively dialyzed (13) whenever nutritionally selective conditions were applied. Powdered modified F12 medium lacking glycine, hypozanthine, and thymidine (F12-GHT) was obtained as a special formulation from Gibco. Growth selection for dhfr-deficient mutants was carried out using a previously described (10) modification of the original method (8). Fluoresceinated methotrexate (F-MTX) was synthesized (14) and generously provided by R.N. Johnston and R.T. Schimke.

Mutagenesis.

The chemical carcinogen N-acetoxy-N-2-acetylaminofluorine (NAAAF) was used as a mutagen to induce dhfr-deficient mutants. UA21 cells ($10^6$) were treated for 2.5 hours with 2 μg/ml of NAAAF in complete medium; this dose kills 80% of the cells. After removal of the mutagen-containing medium, the survivors were plated in two 150 mm dishes and incubated for 6-7 days for expression of the mutant phenotype. Mutants were then selected using either the standard growth selection technique or the FACS, as described below.

Cell sorting.

Cell monolayers, about three-quarters confluent, were exposed to 1 μM F-MTX in a small volume of medium overnight. This concentration of F-MTX was found to be optimal for distinguishing low levels of DHFR from background autofluorescence. The cells were then trypsinized, washed in medium lacking F-MTX, and resuspended in medium at a concentration that ranged from $1-5\times10^5$/ml. The cells were subjected to sorting within four hours, and were protected from strong light during that time. A Becton-Dickenson FACS IV cell sorter with an argon gas laser as an excitation source (488 nm, 500 mwatts) was used; the sample pathway was sterilized with 70% ethanol. Cells were sorted sterilely at a rate of 100-500 per second and collected in 35 mm tissue culture dishes. Fluroescence was analyzed using a series of optical filters as follows: 520 long-pass dichroic, 530 long-pass absorbance, 550 wide-band dielectric; the photomultiplier voltage was 600 volts. Signals were amplified with a linear amplifier and acquired in a pulse-height analyzer. All histograms were transferred to a VAX 11/780 (Digital Equipment Co.) for storage and statistical analysis. All of the histograms presented were produced keeping all gains and other settings constant and using unlabeled cells and fluorescent microspheres (Polysciences #9719) as standards.

DHFR measurement.

DHFR was assayed by [$^3$H]-MTX binding ability as described previously (8).

RESULTS

The level of fluorescence exhibited by dhfr-deficient cells was tested by treating mutant clone DG21 with F-MTX and analyzing the population on the FACS. This mutant represents a double deletion that has eliminated the dhfr locus and contains no detectable DHFR activity (9). There is virtually no background fluorescence bound due to F-MTX (data not shown), since the fluorescence levels are approximately the same as those obtained from untreated cells (FIG. 1A). In contrast, cells of the hemizygous clone UA21, which contain one copy of the dhfr gene, yield a mean flurescence value that is three times higher than this autofluorescence background (FIG. 1B). Thus the FACS can readily distinguish mutant from wild type cells, although there is some overlap between the two distributions.

Cells of clone UA21 were mutagenized with NAAAF and the expressed population was treated with F-MTX and sorted on the FACS. Those cells falling into the bottom 10 percent of the fluorescence distribution were collected, grown for 1-5 days and then subjected to another round of F-MTX treatment and FACS sorting. This procedure was repeated until a total of eight sorts had been completed. Some results of the fluorescence analysis are presented in FIG. 1, panels B-E. After the sixth sort, a significant shift in the fluorescence distribution was evident (FIG. 1D), and after the seventh sort (FIG. 1E), the majority of the cells could be found in a peak corresponding to the background autofluorescence level. At this point the population was plated at low density in non-selective medium and 11 colonies were picked and screened for the DHFR-deficient growth phenotype: the inability to grow in a medium lacking glycine, hypoxanthine and thymidien (the end products of folate metabolism). Ten of the 11 clones tested exhibited the mutant phenotype, in agreement with the indication from the FACS distribution. Cell extracts prepared from two of these mutants were tested for the presence of DHFR activity by the tritiated Methotrexate binding assay. As can be seen in Table 1 both mutants contained no detectable DHFR.

TABLE 1

| DHFR levels in selected mutant clones | | |
|---|---|---|
| Clone | Experiment | Growth in F12-GHT | DHFR level[a] |
| UA21 (parental) | 1 | + | 2.4 |
| DF101 | 1 | − | <0.02 |
| DF102 | 1 | − | <0.03 |
| DF103 | 2 | − | <0.02 |
| DF104 | 2 | − | <0.03 |
| DF105 | 2 | +/− | 1.1 |
| DF106 | 2 | +/− | 1.2 |

[a]P moles [$^3$H]-MTX bound/mg protein

The mutagenesis and sort selection were carried out a second time with similar results. Once again a predominantly dhfr-negative distribution was seen after the seventh sort. Fourteen of 17 clones picked from this population were unable to grow in F12-GHT; the absence of DHFR was confirmed in the two of these clones that were tested (Table 1). The remaining three clones grew poorly in F12-GHT. Two of these clones (DF105 and DF106) were assayed for DHFR; each contains about 50% of the parental level.

During several rounds of the serial sorting a portion of the population was removed and subjected to selection for dhfr-deficient mutants by the standard tritiated deoxyuridine suicide technique. The frequency of mutants in these populations was estimated from the number of colonies surviving the selection protocal. Statistical survival of wild type cells in this selection is approximately $10^{-5}$. As can be seen in Table 2, the serial sorting results in a progressive increase in the frequency fo dhfr-deficient mutants. The initial frequency fo $2-6\times10^{-5}$ is several hundred times higher than the usual spontaneous frequency found in UA21 cells, demonstrating that NAAAF is an effective mutagen in this system. The average enrichment over the course of the experiments was approximately 3-to 5-fold per round, somewhat lower than that expected from the fraction sorted at each round (see Discussion).

TABLE 2

Biochemical selection of dhfr-negative mutants from sorted populations.

| Expt. | Sorted rounds | Cells challenged ($\times 10^{-3}$) | Surviving colonies | Frequency | Enrichment[a] |
|---|---|---|---|---|---|
| 1 | 0 | 150 | 9[b] | $6 \times 10^{-5}$ | 1 |
|   | 2 | 60 | 50 | $8.3 \times 10^{-4}$ | 14 |
|   | 3 | 20 | 66 | $3.3 \times 10^{-3}$ | 55 |
|   | 5 | 8.5 | 1000 | 0.12 | 2000 |
|   | 6 | 0.6 | 100 | 0.3 | 5000 |
| 2 | 0 | 150 | 3 | $2 \times 10^{-5}$ | 1 |
|   | 1 | 60 | 9[c] | $1.5 \times 10^{-4}$ | 7.5 |
|   | 2 | 20 | 10 | $5 \times 10^{-4}$ | 25 |
|   | 4 | 8.5 | 105 | $1.2 \times 10^{-2}$ | 600 |
|   | 5 | 2 | 62 | $3.1 \times 10^{-2}$ | 1550 |

[a]Relative to the original unsorted population.
[b]6/6 clones tested were unable to grow in F12-GHT.
[c]9/9 clones tested were unable to grow in F12-GHT.

DISCUSSION

The availability of a fluorescent ligand that binds to DHFR with great specificity permits the use of the FACS to select mutant mammalian cells that are DHFR-deficient. The selective criterion did not directly involve the catalytic activity of DHFR, but rather was the inability of the cells to accumulate F-MTX in a tightly bound form. Thus one could expect several possible classes of mutants: (1) mutants deficient in both MTX binding ability and catalytic activity (i.e., null mutants); (2) mutants with an altered DHFR with less affinity for MTX but which retains full or partial catalytic activity (e.g. 15, 16); (3) mutants that are unable to transport the drug into the cell (17); (4) mutants that fail to retain MTX within the cell due to a lack of polyglutamylation of folate compounds (18, 19). Mutants of classes 1 and 2 could be expected at relatively high frequency, since the starting cell line used is hemizygous for the dhfr structural gene (9) and so can readily express recessive mutations at this locus. Transport mutants (class 3) would be expected at a much lower frequency since these loci are likely to be diploid and recessive. In fact, over 85% of the mutant clones tested (24/28) displayed the growth characteristics expected of classes 1 or 4. The four of these mutants that were tested lack MTX-binding ability, and so are not in class 4. Thus the majority of mutants isolated in this manner exhibit the expected phenotype of DHFR deficiency. It should be possible to enrich for mutants of class 2 by maintaining the cells in a F12-GHT medium while going through the sorting rounds.

An enrichment of 10-fold was initially expected at each round of sorting, since only the lowest 10% of the fluorescent distribution was collected. The data in Table 2 indicate that an average enrichment of approximately 4-fold was achieved per sorting round. This lower value is probably due to the fact that DHFR-deficient cells grow somewhat more slowly than the wild type and so are selected against during the growth period between sorts.

The FACS selection should be useful for the screening of large populations for DHFR-deficient mutants. The practical limit of the biochemical selection technique is about $10^5$ cells per culture. In order to isolate spontaneous mutants it is necessary to screen $10^7$ cells per culture. This number of cells can be processed on the FACS in 1-2 hours, so it is feasible to screen several populations in one day. Following two rounds of sorting, the population should be sufficiently enriched to allow switching over to the biochemical selection technique.

In most mammalian cells the dhfr gene is expected to be present in at least two copies, as it is in wild type CHO cells (8, 9). Because of this deploidy and the recessive nature of the CHFR-deficient phenotype it has not been possible to select mutants of this type in a single step. Successful isolations in the past have depended on the intermediate isolation of a heterozygote (8) or a hemizygote (9) that carries only a single functional copy of the gene. This first step is a difficult one when starting from wild type cells. Attempts to recover a functional heterozygote or hemizygote mutant of mouse PG19 cells, for example, have been unsuccessful. The FACS method of this invention should make possible the isolation of DHFR-deficient mutants from wild type cells using either of two strategies. First, large numbers of mutagenized cells could be screened directly oro double mutants, which should be present at a frequency of $10^{-7}$ when strong mutagens are used (8). Second, the sorter could be used to enrich for cells in which only one copy of the dhfr gene has been mutated. These heterozygotes contain only one-half the amount of MTX-binding ability (8); the lower half of the fluorescence distribution could be collected at each sort. When the entire population had shifted to this mode, the cells could be mutagenized again and selected for the complete deficiency using the FACS or the biochemical selection method. The isolation of DHFR-deficient mutants in a variety of cell lines is potentially important because of the usefulness of such cells in gene transfer experiments (20, 21).

Most previous applications of the FACS have focused on the isolation of variant cells based on the fluorescence associated with surface macromolecules. In contrast, in the present work the use of the FACS has been extended to the isolation of mutants affected in an internal protein. The FACS was able to detect cells carrying one copy of the dhfr gene. Although this "household" function gene is expressed at a relatively low level, there are still about 300,000 molecules of the enzyme per UA21 cell. The limitation on resolution from negative cells is the autofluorescence of the latter. This background might be reduced by using two lasers: each cell would be analyzed at a second wavelength (at which F-MTX does not absorb); the calculated autofluorescent contribution at the primary wavelength could then be automatically subtracted.

The use of the FACS for the isolation of mammalian cell mutants should be generally applicable whenever a tight-binding fluorescent liqand is available for the gene product. It is also likely that the method could be extended to enzymes for fluorogenic substrates. The ability of the sorter to distinguish partial phenotypes, especially heterozygotes in which the gene product has been reduced by a factor of two, should make this a useful approach for the isolation of mutants affected at diploid loci.

REFERENCES

1. Coffino, P., Baumal, R., Laskov, R., and Scharff, M.D. (1972) J. Cell. Physiol. 79:429–440.
2. Sammons, D. W., Sanchez, E., and Darlington, G.J. (1980) In Vitro 16:918–924.
3. Rosenstraus, M. J., and Chasin, L. A. (1975) Proc. Natl. Acad, Sci. U.S.A. 72:493–497.
4. Stamato, T. D., and Hohmann, L. K. (1975) Cytogenet. Cell Genet. 15:372–379.
5. Esko, J. S. and Raetz, C. R. (1978) Proc. Natl. Acad, Sci. U.S.A. 75:1190–1193.
6. Dangl, J. L., and Herzenberg, L. A. (1982) J. Immunol. Meth. 52:1–14.
7. Miller, A. G. and Whitlock, J. P., Jr. (1981) J. Biol. Chem. 256:2433–2437.
8. Urlaub, G. and Chasin, L. A. (1980) Proc. Natl. Acad. Sci. U.S.A. 77:4216–4220.
9. Urlaub, G., Kas, E., Carothers, A. M. and Chasin, L.A. (1983) Cell 33:405–412.
10. Urlaub, G., Landzberg, M., and Chasin, L. A. Cancer Res. 41:1594–1601.
11. Kaufman, R. J., Bertino, J., and Schimke, R. T. (1978) J. Biol. Chem. 253:5852–5860.
12. Coon, H. G., and Weiss, M. lC. (1960) Proc. Natl. Acad. Sci. U.S.A. 62:852–859.
13. Chasin, L. A., and Urlaub, G. (1976) Somat. Cell Genet. 2:453–467.
14. Johnston, R. N., Beverley, S. M., and Schimke, R.T. (1983) Proc. Natl. Acad. Sci. U.S.A. 80:3711–3715.
15. Flintoff, W., Davidson, S. V., and Siminovitch, L. (1976) Somat. Cell Genet. 2:245–261.
16. Haber, D. A., Beverley, S. M., Kiely, M.L., and Schimke, R.T. (1981) J. Biol. Chem. 256:9510–9510.
17. Flintoff, W., and Saya, L. (1978) Somat. Cell Genet. 4:143–156.
18. McBurney, M. W., and Whitmore, G. F. (1974) Cell 2:173–182.
19. Taylor, R. T., and Hanna, M. L. (1977) Arch. Biochem. Biophys. 181:331–344.
20. Lee, F., Mulligan, R., Berg, P., and Ringold, G. (1981) Nature 294:220–322.
21. Kaufman, R. J., and Sharp, P. A. (1982) J. Mol. Biol. 159:601–621.

What is claimed is:

1. A method of recovering mutant eukaryotic cells which produce a substance encoded by an allelic gene in a quantifiably reduced amount which is about 50% of the amount produced by wild type cells, the mutant cells so recovered being characterized by a mutation in one allele, comprising:
   a. treating wild type cells under mutagenizing conditions so as to produce mutant cells, including mutant cells which produce a substance in a quantifiably, reduced amount relative to wild type cells;
   b. contacting under suitable conditions such mutant cells with a suitable amount of an appropriate detectable compound capable of binding to the substance when it is present in the cells so as to permit the detectable compound to bind to the substance;
   c. detecting the amount of the detectable compound bound to the substance in the cells and thereby the cells which produce the substance in the quantifiably reduced amount; and
   d. recovering such cells which produce the quantifiably reduced amount of the substance.

2. A method of recovering mutant eukaryotic cells producing less than about 10% relative to wild type cells of a substance encoded by an allelic gene, the mutant cells so recovered being characterized by a mutation in both alleles, comprising:
   a. recovering by the method of claim 1 mutant cells which produce about 50% of the amount of the substance produced by wild type cells;
   b. treating the mutant cells so recovered with a mutagen under mutagenizing conditions so as to provide mutant cells which produce the substance in an amount less than about 10% of the amount produced by wild type cells; and
   c. recovering the mutant cells so produced.

3. A method of claim 2, wherein the mutant cells which produce less than about 10% of the amount of the substance produced by the wild type cells are recovered by:
   a. contacting under suitable conditions such mutant cells with a suitable amount of an appropriate detectable compound capable of binding to the substance when it is present in the cells so as to permit the detectable compound to bind to the substance;
   b. detecting the amount of the detectable compound bound to the substance in the cells and thereby the cells which produce less than about 10% of the amount of the substance produced by the wild type cells; and
   c. recovering the mutant cells so produced.

4. A method of claim 2, wherein the recovering comprises culturing the mutagenized cells under suitable conditions for the growth of the mutant cells which produce less than about 10% of the amount of the substance produced by the wild type cells, the suitable conditions being such that the cells recovered in step (a) do not survive.

5. A method of claim 1, wherein the gene which results in production of the substance is present as a single functional gene, the mutant cells recovered are characterized by a mutation in the gene and the quantifiably, reduced amount is less than about 10% of the amount produced by wild type cells.

6. A method of claim 1, wherein the wild type cells are hemizygous.

7. A method of claim 1, wherein the wild type cells are heterozygous.

8. A method of claim 1, wherein the cells are mammalian cells.

9. A method of claim 8, wherein the mammalian cells are Chinese hamster ovary cells.

10. A method of claim 8, wherein the mammalian cells are non-tumorigenic cells.

11. A method of claim 10, wherein the non-tumorigenic cells are African green monkey kidney cells.

12. A method of claim 1, wherein the substance is a protein within the cells.

13. A method of claim 12, wherein the protein is an enzyme.

14. A method of claim 13, wherein the enzyme is dihydrofolate reductase.

15. A method of claim 1, wherein the gene which results in production of the substance in the cells is amplifiable.

16. A method of claim 1, wherein the detectable compound is fluorescent.

17. A method of claim 14, wherein the detectable compound is a fluorescent derivative of methotrexate capable of binding to dihydrofolate reductase under suitable conditions.

18. A method of claim 1, wherein the detecting and recovering are automated.

19. A method of claim 16, wherein the detecting and recovering are accomplished by a fluorescence activated cell sorter.

* * * * *